United States Patent [19]

Pelchy et al.

[11] Patent Number: 5,754,313
[45] Date of Patent: May 19, 1998

[54] IMAGER ASSEMBLY

[75] Inventors: Thomas Edward Pelchy, Moravia; James Edward Grecco, Camillus; Edward Arthur Johnson, Skaneateles; Robert L. Vivenzio; Raymond Albert Lia, both of Auburn; Douglas J. West, Skaneateles; Dominck Danna, Syracuse; Richard L. Bingham, Preble, all of N.Y.

[73] Assignee: Welch Allyn, Inc., Skaneateles Falls, N.Y.

[21] Appl. No.: 682,369

[22] Filed: Jul. 17, 1996

[51] Int. Cl.⁶ .................................................. A61B 1/04
[52] U.S. Cl. .......................... 358/473; 358/482; 348/65; 348/76
[58] Field of Search .............................. 358/471, 473–475, 358/482–484, 901.1; 348/45, 65, 72, 197, 340, 359, 804, 76; 362/32

[56] References Cited

U.S. PATENT DOCUMENTS

| | | | |
|---|---|---|---|
| 4,491,865 | 1/1985 | Danna et al. | 358/98 |
| 4,706,654 | 11/1987 | Ogiu et al. | 128/4 |
| 4,741,327 | 5/1988 | Yabe | 128/6 |
| 4,745,471 | 5/1988 | Takamura et al. | 358/98 |
| 4,757,805 | 7/1988 | Yabe | 128/6 |
| 4,786,965 | 11/1988 | Yabe | 358/98 |
| 4,918,521 | 4/1990 | Yabe et al. | 358/98 |
| 5,021,888 | 6/1991 | Kondou et al. | 358/213.11 |
| 5,051,824 | 9/1991 | Yabe et al. | 358/98 |
| 5,305,098 | 4/1994 | Matsunaka et al. | 348/65 |
| 5,587,736 | 12/1996 | Walls | 348/65 |

*Primary Examiner*—Edward L. Coles, Sr.
*Assistant Examiner*—Stephen Brinich
*Attorney, Agent, or Firm*—Wall, Marjama & Bilinski

[57] ABSTRACT

A solid state imager assembly for use in an insertion tube of a video endoscope that includes a TAB imager package having fine pitch leads extending outwardly to either side of the imager. A transparent window covers the imager. A first hybrid board is attached to one set of leads and a second hybrid circuit board is attached to the second set of leads. The boards are turned downwardly to either side of the imager and placed in opposed parallel alignment beneath the imager. Circuitry is mounted on the opposed inside surfaces of the boards. A block of encapsulating material is placed between the boards to encapsulate the circuitry therein and provide structural support to the package.

29 Claims, 6 Drawing Sheets

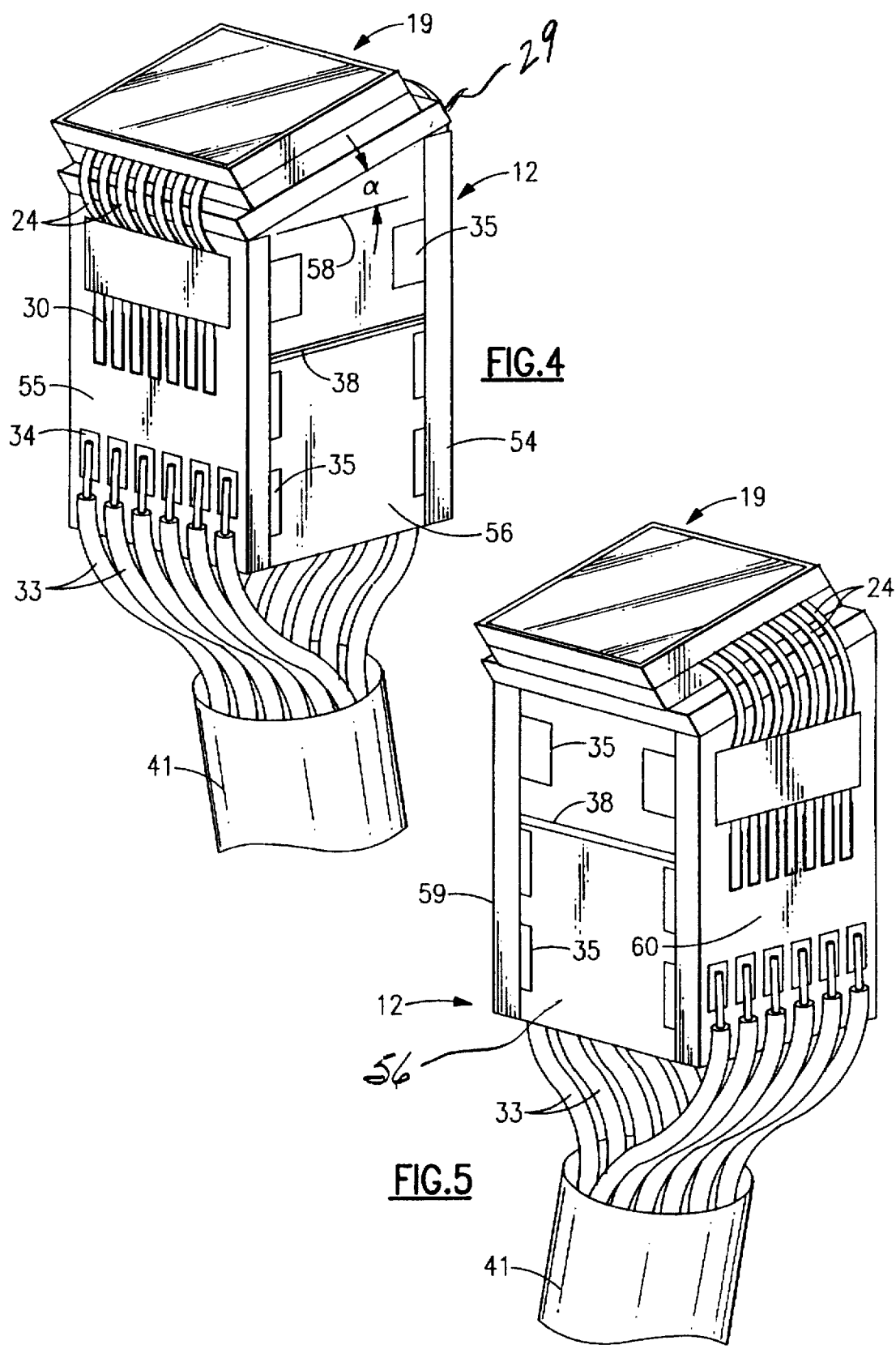

IMAGER ASSEMBLY

BACKGROUND OF THE INVENTION

This invention relates to a solid state imager assembly and, in particular, to a highly compact imager assembly suitable for use in a video endoscope.

The increased availability of smaller solid state imagers based on CCD or CMOS technologies has surpassed the ability of conventional wire bonding techniques to take full advantage of the space savings afforded by these small imagers. An advanced integrated circuit technology known as the tape automated bonding (TAB) process has been developed which permits fine line high pitch lead patterns to be bonded to extremely small electronic components such as CCD imagers. In this process the imager is supported on a thin flexible substrate and the high density imager leads are TAB die bonded to the substrate. The high pitch leads typically extend outwardly from both sides of the imager for a distance sufficient to allow the leads to be connected to other electrical components using more conventional bonding techniques. A transparent window, typically being glass, is placed over the imager and the extended leads to complete the package. This package will be herein referred to as a TAB imager or TAB imager package.

TAB packages are structurally relatively weak and are normally mounted on a flat support such as an IC board, along with other electrical components. The TAB boards, however, are rather bulky and space consuming and thus do not lend themselves for use in confined regions such as in the camera head of a video endoscope.

SUMMARY OF THE INVENTION

It is therefore an object of the present invention to improve the packaging of solid state imagers It is a further object of the present invention to improve the packaging of a solid state imager unit employing the TAB bonding process.

A still further object of the present invention is to further compact imager and board assemblies used in the insertion tube of a video endoscope.

Another object of the present invention is to decrease the size of an insertion tube used in a video endoscope.

Yet another object of the present invention is to provide a compact camera head for a video endoscope that is both rugged and insensitive to changes in ambient conditions.

A further object of the present invention is to provide a compact TAB imager unit that can be mounted at an angle with regard to the central axis of an insertion tube of a video endoscope to create additional space within the insertion tube.

These and other objects of the present invention are attained by means of a solid state imager assembly suitable for use at the distal end of an insertion tube used in a video endoscope. The assembly includes a TAB imager covered by a transparent window and further including pitch leads being between 0.010 and 0.20 inches. A first circuit board is attached to one set of leads while a second circuit board is attached to the other set of leads. The boards are turned downwardly to either side of the imager so that they are in parallel alignment beneath the image. Circuitry is mounted on the inside of the aligned boards and a block of encapsulating material is placed between the boards which covers the electrical circuitry on each of the boards. At least the inside surfaces of the boards are bonded to the encapsulating material to secure the boards in assembly. In one form of the invention, the TAB imager package is mounted on a substrate that is seated upon the top edges of the hybrid boards. The substrate is bonded either to the boards or the encapsulating block to provide additional structural integrity to the assembly.

BRIEF DESCRIPTION OF THE DRAWINGS

For a better understanding of these and other objects of the present invention, reference will be made to the following detailed description of the invention which is to be read in association with the following drawings, wherein:

FIG. 4 is an enlarged perspective view of an imager assembly showing the imager mounted at an acute angle with regard to the vertical axis of the assembly upon a block of encapsulating material with the imager leads being connected to a pair of opposed circuit boards vertically disposed beneath the imager and being bonded to the front and rear end walls of the encapsulating block;

FIG. 5 is an enlarged perspective view of an imager assembly showing the imager mounted at an acute angle with regard to the vertical axis of the assembly upon a block of encapsulating material with the imager leads being connected to a pair of opposed circuit boards vertically disposed beneath the imager and being bonded to the opposing two side walls of the encapsulating block;

DESCRIPTION OF THE INVENTION

Figure 10:
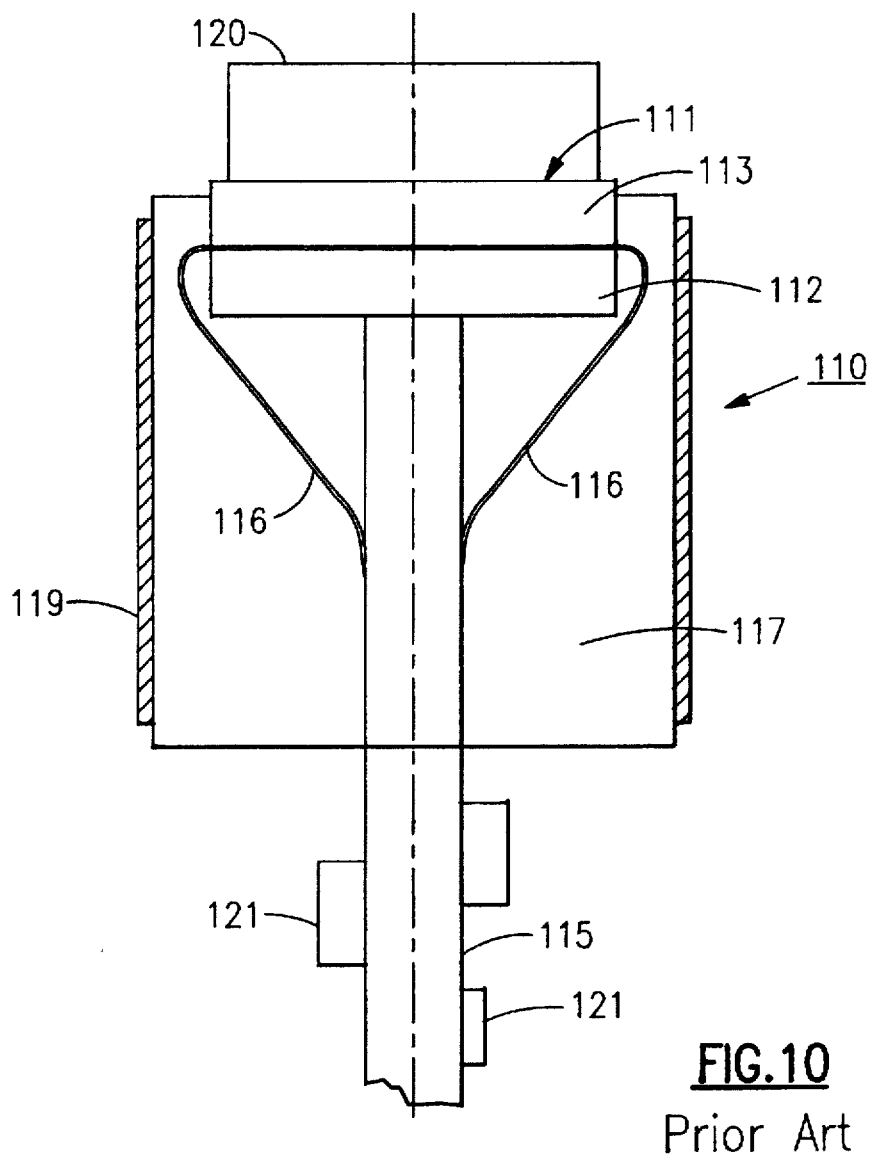
FIG. 10 is an enlarged side elevation showing a prior art imager package.

Turning initially to FIG. 10, there is shown a prior art TAB imager assembly generally referenced 110. The assembly includes a TAB imager package 111 that includes a solid state imager 112 which is protectively covered with a transparent window 113. The imager package is centrally mounted upon the top edge of an elongated circuit board 115. The imager leads 116, which extend outwardly from between the window and the imager to both sides of the imager are turned downwardly and are bonded to either side of the circuit board. A block 117 of epoxy resin is placed about the imager package and the circuit board to bond the two together in assembly. The block of resin is enclosed in a metal band 119 and a second glass window 120 is placed over the imager. Circuit means 121—121 are contained on either side of the circuit board and is connected to the leads by suitable electrical traces.

Although the prior art TAB imager package is somewhat compacted in width when compared to similar packages, it nevertheless is relatively greater in length. Because of the extended length, the prior art package does not lend itself for use in a video endoscope wherein the distal end of the insertion tube must be articulated to maneuver the tube around sharp corners or bends.

Figure 1:
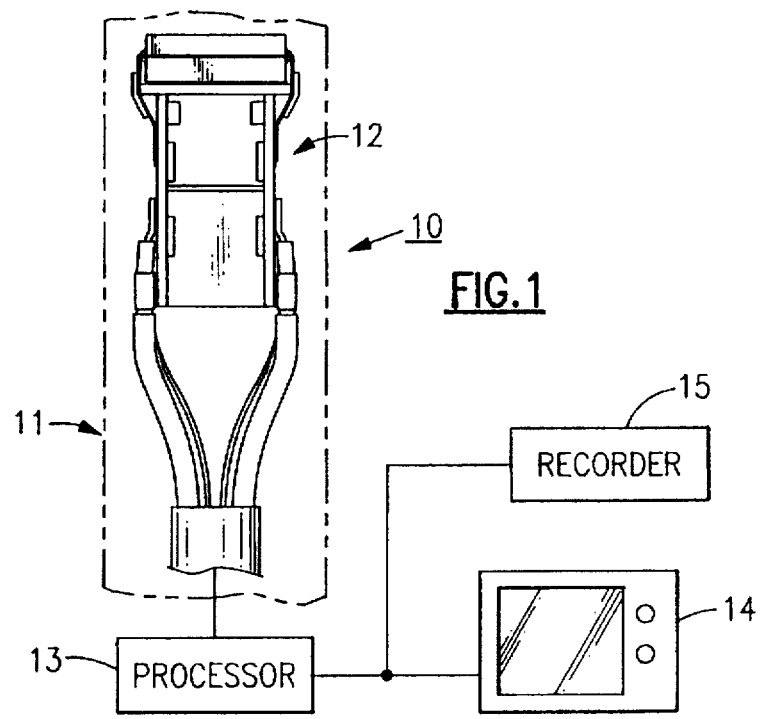
FIG. 1 is a schematic view showing the component parts of a video endoscope embodying the teachings of the present invention.

Referring now to FIG. 1, there is shown in schematic form a video endoscope embodying the teachings of the present invention. The system 10 includes an elongated insertion tube 11 having a small solid state imager assembly 12 mounted at its distal end that is capable of recording an image of a target located within the viewing range of the imager. The recorded image data is converted to electrical read out signals that are sent via the insertion tube to a video processor 13 where the signals are placed in a format for either direct viewing by a video monitor 14 or for storage for later viewing in a video recorder 15.

Although not shown, the insertion tube is provided with a steering capability that permits the distal end of the tube that houses the imager assembly to be articulated. Other functional components that are well known in the art may also be provided, such as lighting to illuminate the target region and an air and water delivery system for carrying out different procedures, particularly many procedures needed in medical applications.

Since the commercial introduction of video equipped endoscopes in the early 1980's, the trend in the industry has been towards reducing the size of the imager assemblies used in these instruments. Advances in electronics have made available extremely small CCD imagers and electronic components for servicing the imagers. As noted above, small CCD imagers having fine pitch leads which are 2 mm or less are now manufactured using the tape automated bonding process (TAB) wherein the imager is mounted upon a thin film-like support surface and covered with a transparent protective window which is typically glass. Because of the small size of the imager, the lead patterns to and from the imager must be compacted.

Heretofore, the TAB imager assemblies, which are relatively weak structurally, have been placed on more substantial flat IC boards and the lead connected to appropriate traces on the board leading to input and output circuits mounted on the board. As should be evident, this type of flat packaging is space consuming and thus does not lend itself for use in a confined area such as the distal head of a video endoscope insertion tube.

Figure 2:
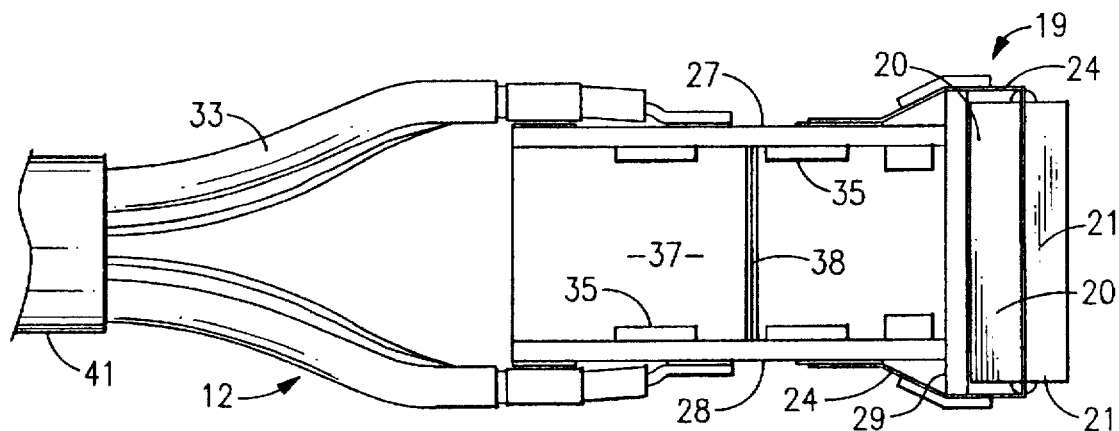
FIG. 2 is an end view showing the imager assembly utilized in the endoscope shown in FIG. 1.
Figure 3:
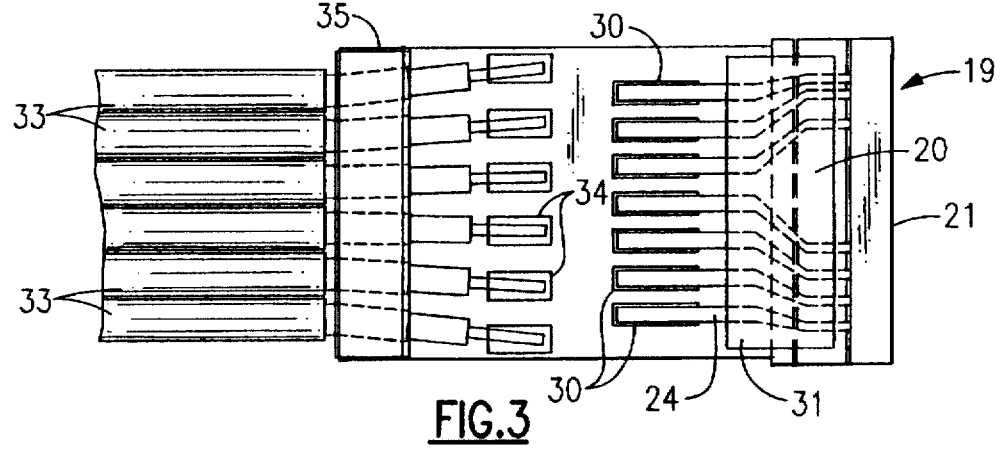
FIG. 3 is a side view of the imager assembly shown in FIG. 2.

Referring now to FIGS. 2 and 3, the imager assembly of the present invention includes a TAB imager package generally referenced 19 that includes a CCD imager and a glass window 21 mounted thereover to protect the imager recording surface of the imager. A series of high density leads 24—24 pass from between the imager and the window and extend outwardly to either side of the imager. The pitch between leads is at or less than 2 mm. Unlike the conventional mounting on a flat IC board, the present imager package is connected to parallelly align circuit boards 27 and 28 mounted beneath the imager in general perpendicular alignment therewith. The boards are brought inside the side margins of the imager assembly. Each board has a width that is about equal to the end-to-end width of the imager assembly and are positioned at or inside the end margin of the assembly. The boards are constructed of a very thin non-conductive material in order to save space, the thickness of each board being between 0.010 inches and 0.020 inches. Accordingly, the circuit boards add little structural strength to the assembly.

In this embodiment of the invention, the entire imager assembly is mounted upon a non-conductive substrate 29 which, in turn, is seated symmetrically upon the top edges of the boards. Here again, the substrate, like the boards, are about 0.010 and 0.020 inches thick. The substrate slightly overlies the boards, and the leads extending from the imager assembly are brought down around the substrate and are bonded to traces 30—30 on the outside faces of the boards. As best seen in FIG. 3, the high pitch lead patterns are fanned out at the distal end of each array so that the free ends of the leads can be solder bonded to the traces using conventional bonding techniques. A protective strip 31, which in this case, is a residual part of the original TAB packaging, is situated over each lead array in the bend region to provide additional protection to the leads and hold them in proper alignment.

Transmission wires 33—33 that extend back through the insertion tube are similarly solder bonded to traces 34—34 located on the outer faces of the two hybrid boards. Circuit components 35—35 are mounted on the inside faces of the two boards and the components are connected to appropriate traces to permit input and output signals to be efficiently exchanged between the imager and the processor. Here again, a protective strip 36 is mounted over the wires at the back of the boards to protect the wires and to help maintain them in alignment.

As noted above, the structural components of the imager assembly are relatively thin and weak and the entire assembly is extremely difficult to handle, particularly during assembly of the insertion tube. The imager unit thus poses a constant danger of becoming misaligned at any time during assembly, thus adversely effecting the operability of the instrument. Any misalignment of the imager may, in fact, render the instrument unsuitable for use. In order to provide the imager package with the required structural strength, an encapsulating material is placed within the space between the two hybrid boards. Preferably, the material is an epoxy resin that can be applied s a liquid and which cures into a solid block 37. The resin is applied so that it completely blankets the circuit components mounted on the back of the boards. In addition, the resin wets the back of both of the hybrid boards and the substrate upon which the TAB imager package is mounted. As a result, all of the components of the imager assembly become tightly bonded together when the resin cures. This not only protects the electric board components, but also provides structural strength and integrity to the assembly.

As illustrated in FIG. 2, one or more lines 38 may be extended through the resin block to connect the circuitry mounted on one hybrid board with circuitry mounted on the other board. In this embodiment, the line or lines are contained below the surface of the block within a recess formed in the block. The lines, however, may be completely encapsulated in the resin to provide additional protection to the lines or brought around the resin block beneath the substrate that supports the image package.

Figure 8:
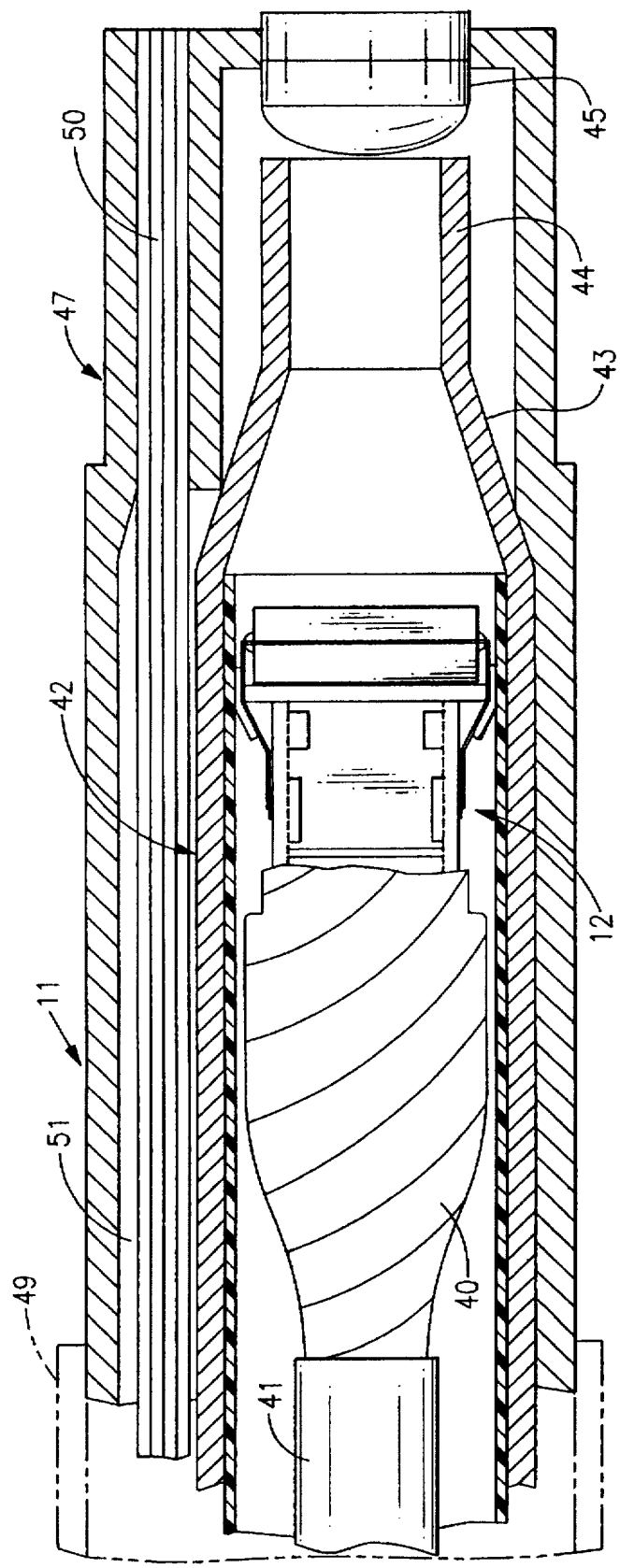
FIG. 8 is an enlarged side elevation showing the distal end of the insertion tube of a video endoscope embodying the teachings of the present invention.
Figure 9:
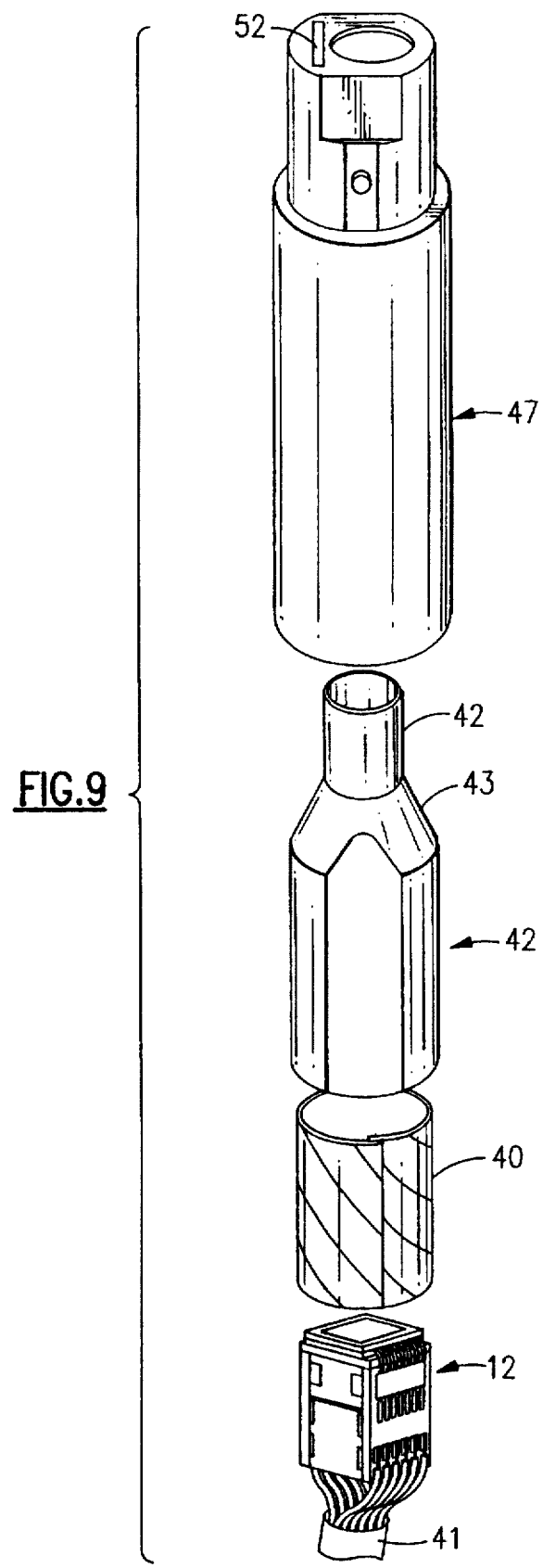
FIG. 9 is an exploded view showing the component parts of the imager assembly shown in FIG. 8.

Turning now to FIGS. 8 and 9, the imager assembly 12, as described with reference to FIGS. 2 and 3, is shown mounted in the distal end of an insertion tube 11. Initially, the body of the imager assembly and the transmission wires are wrapped with a heat shrinkable Mylar tape 40 and the wire bundle is passed into a sheath 41. The imager window remains unwrapped so that it is able to clearly view a target positioned in front of the insertion tube. The wrapped imager package is then placed within a very thin walled cylindrical container 42 made of nickel that fits closely about the imager assembly. The container has a necked down section 43 that enters a smaller cylindrical front section 44. The front section of the container is positioned in assembly adjacent to a lens system 45 mounted in the front distal face of an outer housing 47. The lens system may have one or more lens elements that ar arranged to focus a target image upon the recording surface of the imager.

The housing 47 is placed over the nickel container as illustrated in FIG. 8 and is secured to the outer casing 49 of the insertion tube 11. A light carrying fiber bundle 50 is arranged to pass through an axially disposed channel 51 in the housing. The fiber bundle carries light through an exit port 52 into the target viewing region of the instrument.

As described in U.S. Pat. No. 4,980,763 to Lia, a video endoscope is adapted to provide accurate measurement readings within the target region of the instrument. This method involves the generation of a shadow in the plane of the target to provide reference data upon which certain dimensional calculations relating to size and distance can be based. It is desirable in this type of application, as well as other applications to offset the imager at a slight angle with regard to a plane normal to the axis of the imager assembly. By tilting the imager slightly within the insertion tube, additional space is gained within the distal tip region that can be utilized to accommodate various instrument components.

The present imager assembly lends itself ideally to this tipped imager configuration. A tipped imager assembly embodying the teachings of the present invention is illustrated in FIG. 4 wherein a pair of opposed hybrid boards 54 and 55 are encapsulated within a block of epoxy resin 56 to protect the electrical components 57 mounted on opposed inner surfaces of the boards. The top surface of the resin block is placed at an angle $\alpha$ with respect to a plane 58 which is normal to the axis of the assembly. A TAB imager package 19 is seated upon the top surface of the epoxy block and, like the circuit boards, the substrate 29 of the package is bonded to the block to provide structural integrity to the structure in assembly.

Here again, the imager leads 24—24 and the transmission wires 33—33 are connected to the board traces 30 and 34, respectively. In this embodiment of the invention, the imager is tilted downwardly from the back to the front of the assembly with the hybrid boards being bonded to the front and back surfaces of the epoxy resin block.

In certain applications, it may be desirous to change the imager orientation with regard to the imager assembly. FIG. 5 illustrates a further embodiment of the invention wherein the hybrid boards 59 and 60 are bonded to the opposing side wall surfaces of the epoxy resin block 56 and the TAB imager package 19 is rotated 90° with respect to the orientation shown in FIG. 4. Turning the imager package will reorientate the imager provided by the imager to the processor.

Figure 6:
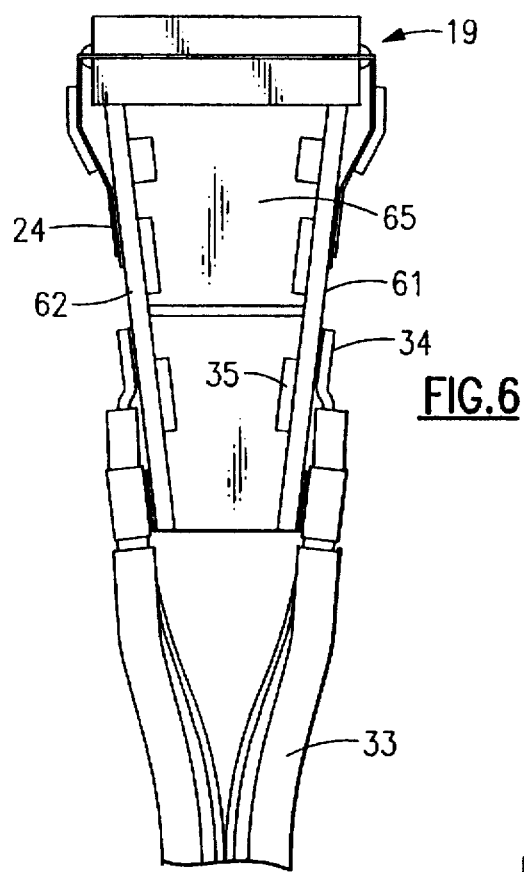
FIG. 6 is an end view of a further embodiment of an imager assembly embodying the teachings of the present invention.

FIG. 6 is a further embodiment of the invention wherein the same numbers as used above are used to identify like components. In this embodiment the hybrid boards 61 and 62 are inclined inwardly from the TAB imager package 19 toward the transmission wires 33—33. Again, the hybrid boards are bonded to a tapered block 65 of resin. The TAB imager package is placed directly in contact with the top of the block and the bottom surface of the package is also bonded to the block. The bottom surface of TAB package is typically "active" in that unshielded electrical components or the like are exposed along the bottom surface of the package. By bonding or partially encapsulating the bottom surface of the TAB package in the resin block, the active electrical components located on the bottom surface of the TAB package are well protected and the need of a substrate is eliminated.

Figure 7:
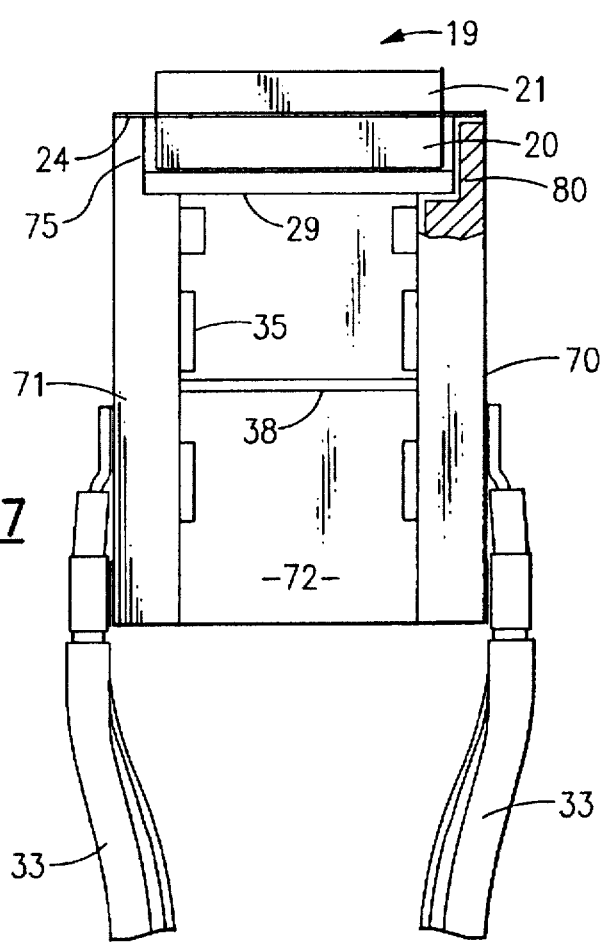
FIG. 7 is an end view of another embodiment of an imager assembly embodying the teachings of the present invention.

FIG. 7 relates to another embodiment of the present invention. A pair of opposed hybrid boards 70 and 71 are separated by a block of epoxy resin 72. The boards are bonded to the block by adhering the resin to the board surfaces. Recessed shoulders 75—75 are formed along the inside top edges of the board. The TAB imager package 19 is mounted upon a substrate 29 and the substrate, in turn, is arranged to rest on the bottom walls of the opposed shoulders. The depth of each shoulder is substantially equal to the combined height of the substrate 29 and the imager 20. As a result of this arrangement, the imager leads 24 extend outwardly from the imager package over the top edge surfaces of the boards. Traces 80 are provided along these surfaces that pass downward along the shoulders to the electrical circuits carried on the inside of each board. The leads are bonded to the traces and trimmed to the required length. Although the leads are shown bonded to traces running along the top surfaces of the hybrid boards, the leads may also be bent downwardly along the outside of the boards and bonded to traces located on the outer face of each board as illustrated in FIGS. 2 and 3.

While this invention has been explained with reference to the structure disclosed herein, it is not confined to the details set forth and this invention is intended to cover any modifications and changes as may come within the scope of the following claims:

What is claimed is:

1. A solid state imager assembly that includes a TAB imager unit having a transparent window mounted over a solid state imager; a first set of imager leads passing outwardly from between the imager and the window to one side of the unit and a second set of imager leads passing outwardly from between the imager and the window to the other side of the unit, a first circuit board solder bonded to the first set of leads and a second circuit board solder bonded to said second set of leads, said first and second circuit boards containing circuit components positioned in spaced apart alignment beneath said imager unit with the inside surfaces of the boards facing each other, and a block of encapsulating material at least partially encapsulating to said boards and filling the space between said boards to support the boards in alignment.

2. The solid state imager assembly of claim 1 that further includes electrical components mounted on the inside of said boards, said components being contained within said encapsulating material.

3. The solid state imager assembly of claim 2 that further includes means for connecting at least one electrical component mounted on one board being with an electrical component mounted on the other board.

4. The solid state imager assembly of claim 1 that further includes transmission wires attached to the boards for electrically coupling said boards to a remote video processor.

5. The solid state imager assembly of claim 1 where the thickness of each circuit board is about between 0.010 and 0.020 inches.

6. The solid state imager assembly of claim 1 that further includes a substrate for supporting the imager unit that is mounted upon the top edge surfaces of said aligned boards so that said substrate spans the space between the boards.

7. The solid sate imager assembly of claim 6 wherein said substrate is at least partially encapsulated in said encapsulating material.

8. The solid state imager assembly of claim 1 wherein the side walls of the encapsulating block are in parallel alignment.

9. The solid state imager assembly of claim 1 wherein said side walls of the encapsulating block taper inwardly from the top wall of the block to the bottom wall of the block.

10. The solid state imager assembly of claim 1 wherein said block is rectangular in form having opposed side walls to which said boards are bonded and opposed front and back end walls.

11. The solid state imager assembly of claim 10 wherein the top wall of said encapsulating block is inclined at an angle with regard to an opposed pair of sidewalls and the solid state imager package is seated upon the inclined top wall of said block.

12. The solid state imager assembly of claim 11 wherein said top wall of said block slants downwardly from one side wall to the other.

13. The solid state imager assembly of claim 11 wherein said top wall of said block slants downwardly from one end wall toward the other end wall.

14. The solid state imager assembly of claim 5 wherein the pitch between leads is 2 mm or less.

15. A solid state imager assembly that includes
- a pair of circuit boards positioned in spaced apart alignment, said boards having opposed inner faces, outer faces and top edge surfaces, each board having a shoulder formed to a desired depth in said top edge surface of said boards so that the shoulders face each other,
- a TAB imager unit seated in said recesses so that the unit spans the space between the boards, said unit including a solid state imager and a transparent window mounted over the imager, the height of the imager being about equal to the depth of the shoulders and being seated therein,
- a first set of imager leads passing outwardly from between the imager and the window to one side and extending over the top edge surface of one of said boards and a second set of imager leads passing outwardly from between the imager and the window to the other side of the unit extending over the top edge surface of the other board,
- circuit traces printed on each of the boards, and
- means for electrically connecting the leads to said traces on said boards.

16. The imager assembly of claim 15 that further includes a block of encapsulating material positioned between said boards, said boards being at least partially encapsulated in said material.

17. The imager assembly of claim 16 that further includes electrical circuit means mounted on opposed inner faces of said boards, said circuit means being encapsulated within said material.

18. The imager assembly of claim 17 wherein the leads are bent downwardly over the top edge surfaces of the boards and are bonded to traces on the outer faces of said boards.

19. The imager assembly of claim 17 that includes traces passing along the top edge surfaces of said boards in spaced apart alignment beneath said leads and said leads are bonded to to said traces.

20. The imager assembly of claim 17 that further includes transmission wires connected to the board for coupling the boards electrically to a remote video processor.

21. The imager of claim 17 that further includes at least one electrical line passing between the boards for electrically interconnecting electrical circuit means on said boards.

22. The imager of claim 17 that further includes a substrate mounted in said recesses upon which the imager package is supported said substrate being partially encapsulated within said material.

23. A video endoscope having a video processor connected to an insertion tube for generating video images of a target, said endoscope further including,
- a housing mounted in the distal end of the insertion tube,
- a light bundle contained in said housing having a light exit face at the distal end of the insertion tube,
- a lens means mounted in the housing for focussing an image of a target within a plane located inside said housing,
- a TAB imager that includes a solid state imager having an image recording surface and a transparent window mounted over the imager, said unit being mounted in said housing behind the lens with the image recording surface of the imager lying in the focal plane of the lens means,
- a first set of imager leads passing outwardly from between the imager and the window to one side of the unit and a second set of imager leads passing outwardly from between the imager and the window to the other side of the unit,
- a first circuit board connected to said first set of leads and a second circuit board connected to said second set of leads, each board having an inner face and an outer face and a top edge surface,
- said first and second circuit boards positioned in spaced apart relationship behind said imager unit with the inner surfaces of said boards facing each other, and
- a block of epoxy resin mounted between said boards with said boards being at least partially encapsulated in said resin.

24. The endoscope of claim 23 that further includes electrical circuit means mounted upon the inner faces of said boards, said circuit means being encapsulated in said encapsulating material.

25. The endoscope of claim 24 that further includes a substrate mounted upon the top edge surfaces of said boards and said imager unit being mounted upon said substrate and, said substrate being partially encapsulated in an epoxy resin.

26. The endoscope of claim 25 wherein said leads are bent downwardly over said substrate and are bonded to a first group of traces located upon the outer faces of each board.

27. The endoscope of claim 26 that further includes transmission wires passing inwardly through the back of said housing, said wires being bonded to a second group of traces located upon the outer faces of each board for electrically connecting said boards to a remote video processor.

28. The endoscope of claim 27 wherein the transmission wires are contained within a protective sheath.

29. The endoscope of claim 24 that further includes at least one electrical line for placing circuitry on one board in communication with circuitry on the other board.

\* \* \* \* \*